United States Patent [19]

Pagano

[11] Patent Number: 4,785,668
[45] Date of Patent: Nov. 22, 1988

[54] DRILL COLLAR TESTER

[76] Inventor: Dominick A. Pagano, 10 Sasqua Trail, Weston, Conn. 06883

[21] Appl. No.: 38,134

[22] Filed: Apr. 14, 1987

[51] Int. Cl.⁴ ............................................. G01N 29/00
[52] U.S. Cl. ........................................ 73/622; 73/637
[58] Field of Search ................. 73/622, 623, 629, 633, 73/634, 637, 638

[56] References Cited

U.S. PATENT DOCUMENTS 3,977,236  8/1976  Raatz, Jr. et al. ..................... 73/622
4,597,294  7/1986  Brill, III et al. ...................... 73/623

Primary Examiner—John Chapman
Assistant Examiner—Louis M. Arana
Attorney, Agent, or Firm—Lieberman Rudolph & Nowak

[57] ABSTRACT

The instant invention relates to an apparatus and method for inspecting the structural integrity of drill collars used in the drilling of oil and gas wells.

5 Claims, 2 Drawing Sheets

DRILL COLLAR TESTER

FIELD OF THE INVENTION

The instant invention relates to an apparatus and method for checking the structural integrity of drill collars used in the drilling of oil and gas wells. Drill collars are used to connect the drill bit to the drill stem and also to apply weight to the drill bit. As many as thirty or more collars might be included in the total length of the drill stem to apply weight to it, thereby promoting efficient and vertical drilling.

Each collar has two couplings, a threaded "male" coupling on one end called a "pin" and a threaded "female" coupling on the opposite end called a "box". The collars are screwed together by mating their couplings with complimentary couplings on the drill bit and other portions of drill pipe.

Large stresses are placed upon these unions, and when a well gets to substantially deep, comprising many lengths of similarly joined pipe, the reliability of these unions becomes critical An undetected defect in either the "pin" or the "box" wall strcuture, can lead to the coupling shearing off resulting in the loss of the drill bit and the portions of drill pipe remaining in the ground. This could necessitate a costly extraction procedure and might even lead to the abandonment of the well.

The present invention described an inexpensive yet thorough method for automatically examining the structural integrity of drill collar couplings and represents a significant improvement over the prior art, providing a repeatable and highly accurate method of scanning the coupling of the drill collar under computer control. The generic term coupling is used interchangeably herein with the terms "pin" and "box".

DESCRIPTION OF THE PRIOR ART

Enormous stresses are placed upon drill collars as an oil or gas well is drilled, and periodic examination of the "pin" and "box" couplings are crucial in order to prevent loss resulting from structural failure. Common methods of inspection include the use of magnetic particles, which are dusted over the surface of the couplings in order to reveal surface defects upon application of a magnetic field to the pipe; or the use of dye penetrants, which are painted or applied to the surface of the coupling and caused to fluoresce, thereby, revealing any surface defects. Serious problems arise in using these surface methods, however, in that a defect might be internal to the wall of the coupling and not present on its surface. In addition. these methods will not reveal the depth of a surface crack.

The use of ultrasonic pulse echo technology in detecting defects in structures is well known. U.S. Pat. No. 3,415,110 to Cowan describes the use of an electromechanical transducer, acoustically coupled to a workpiece. The transducer transmits a mechanical wave of ultrasonic frequency which is passed into the material of the workpiece. Any discontinuity within the workpiece reflects the mechanical wave generating an echo which is received by the transducer. The use of gating, counting and timing circuits are employed to evaluate the size of a defect and its location. U.S. Pat. No. 4,222,275 to Sholl et.al. teaches the use of digital computers to control the transmission of the ultrasonic wave and the analysis of the received echo. The disclosures of these patents shall be incorporated herein by reference.

Hand held ultrasonic testers have been used with some success in checking for defects, however, control of scanning with hand held devices is limited and can result in incomplete analysis of the coupling under test.

Quick connect-disconnect mechanisms for attaching apparatus to threaded members, of the type used in the instant invention, are well known in the art.

It is, therefore, an object of the instant invention to provide an apparatus for checking the structural integrity of a drill collar "box" or "pin" coupling.

It is a further object of the invention to provide a thorough computer controlled method of detecting internal as well as external defects in the walls of a drill collar coupling, and discerning the size and location of each defect.

It is a still further object of the present invention to provide an apparatus which can be used to create B and C type two dimensional computer scans of the walls of the drill collar coupling.

SUMMARY OF THE INVENTION

The instant invention consists of a transducer mounted on a platform which in turn is supported by cam followers which ride on the mouth of a threaded drill collar coupling, be it "box" or "pin". Electrical stimulation of the transducer causing the transmission of ultrasonic waves is provided and controlled by a computer. Analysis of the echoes received by the transducer is also provided by the computer.

Rotation of the transducer around the mouth of the coupling is facilitated by a stepper motor, which responds to positional signals provided by the computer. The stepper motor causes the platform to angularly rotate in response to electrical signals from the computer and allows a complete 360 degree scan under computer control. This computer controlled inspection provides substantial improvement over a hand held inspection in that the rotational movement is sequentially controlled by instructions stored digitally in the computer memory and the scan angle is kept constant due to the transducer being firmly, but adjustably positioned on the rotating platform.

The computer accurately controls rotation of the platform in synchronization with the internal clock of the computer. The transmission of the ultrasonic waves and reception of the echoes are similarly controlled by the computer and hence are synchronized to the internal clock of the computer. This synchronization of the rotational movement of the transducer and the transmission and reception of the ultrasonic waves by the computer enables the computer to accurately record not only the presence of a defect, but its depth and size with respect to the circumference of the "pin" or "box" coupling being tested.

Water is used as an acoustical couplant between the transducer and the surfaces of the drill collar coupling. The water is continuously supplied by a hose connected to the transducer and drains through the drill collar being tested.

It is, therefore, a feature of the present invention to provide a method and apparatus for checking the structural integrity of the "pin" and "box" coupling of a drill collar using a computer controlled rotating transducer.

It is a further feature of the present invention that the transducer rides adjacent to the circumference of the mouth of the coupling and scans the coupling wall at a constant angle in order to detect defects in the coupling wall.

It is a further feature that the angle of transmission by the transducer is adjustable.

It is a still further feature of the invention that the results of the computer controlled rotation, scan and analysis can be used to constrtuct a two-dimensional plot showing both the depth and size of any internal or external defect in the coupling wall.

These and other objects and features of the present invention will become more apparent when taken in conjunction with the following detailed description and drawings wherein like characters indicate like parts.

DETAILED DESCRIPTION OF THE INVENTION

Figure 1:
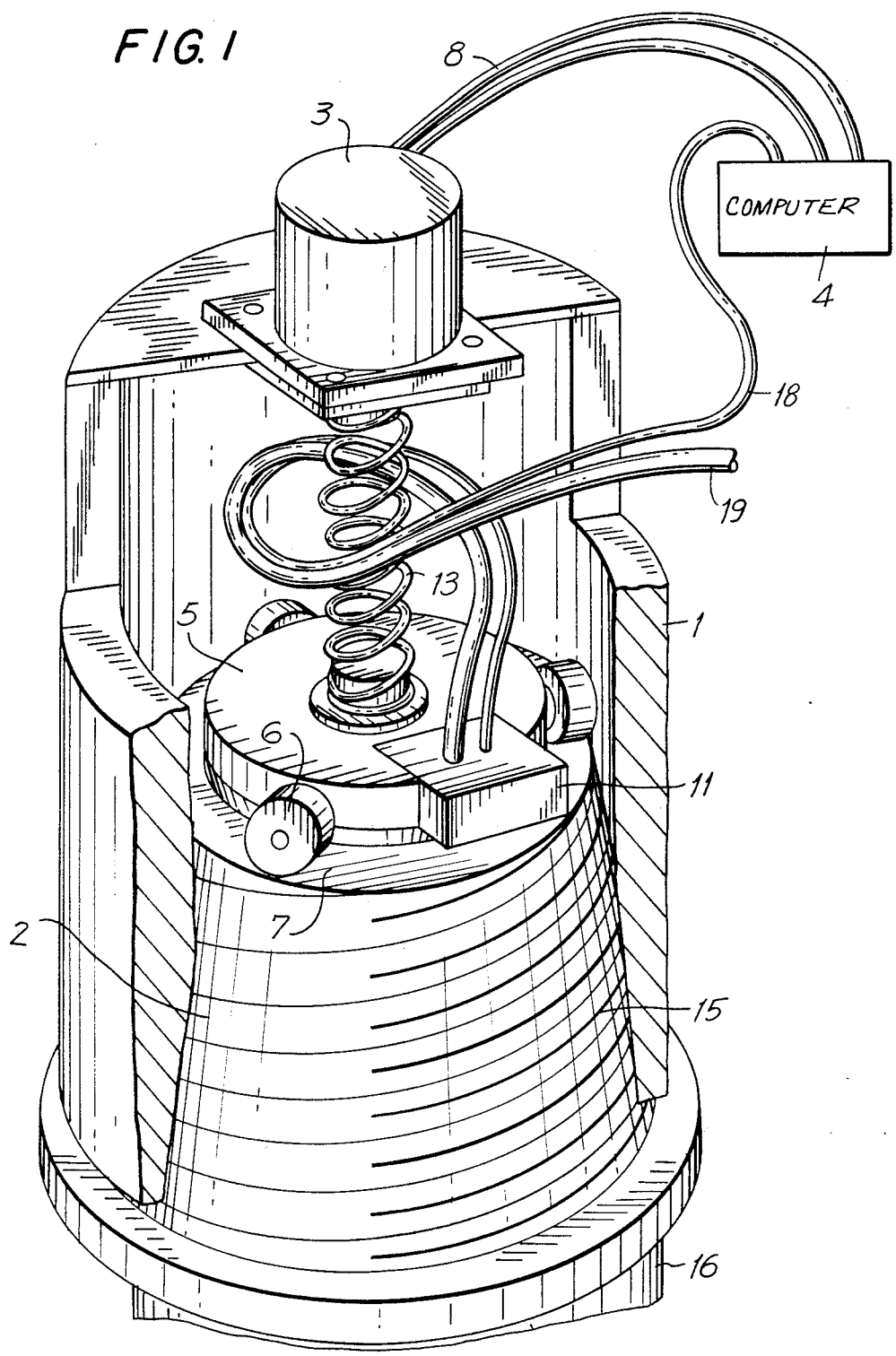
FIG. 1 is an isometric, partially sectional view of one embodiment of the present invention.
Figure 2:
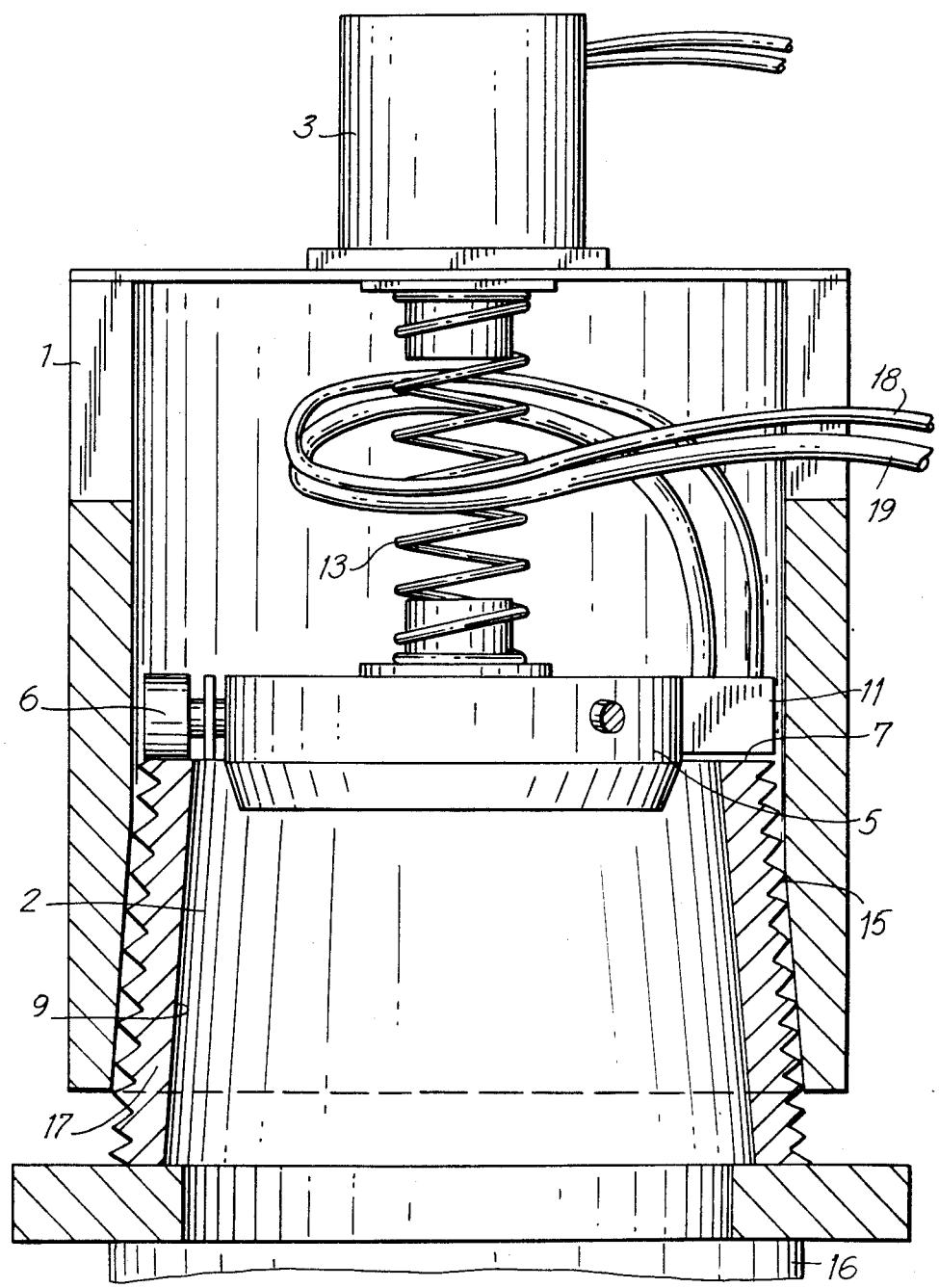
FIG. 2 is a sectional side view of the apparatus shown in FIG. 1.

Referring now to FIGS. 1 and 2 there is shown the "pin" coupling 2 of a drill collar. The "pin" is threaded in order to facilitate engagement with a corresponding "box" of a piece of drill pipe, a drill bit or another drill collar. Mounted thereupon are components of one embodiment of the instant invention, used for inspecting the "pin" of the drill collar. Shown are a tester housing 1 which is provided with an internal structure (not shown) which allows its quick, yet secure connection to the threads of pin 2 without screwing thereupon. This type of structure, known as a "quick connect-disconnect" is well known in the prior art. An electrically activated stepper motor 3 is shown mounted to the top surface of housing 1 and connected via cable 8 to a computer 4 shown in block diagram form.

Transducer platform 5 is movably mounted within the housing 1 upon a plurality of rotating cam followers 6 which rest upon the highly machined mouth 7 of the coupling 2. Mouth 7 is substantially perpendicular to the longitudinal axis of the drill collar coupling 2. Ultrasonic transducer 11 is mounted upon platform 5, positioned slightly above and in alignment with the circumference of mouth 7 of the coupling. Its rotation around the circumference of mouth 7 is controlled by the rotation of platform 5 which is in turn controlled by stepper motor 3 which is mounted on the outer upper portion of the housing 1.

In operation, the housing 1 engages the coupling 2, so that platform 5 is seated on the coupling mouth 7. A computer 4 is programmed to provide a sequence of electrical positional signals to the stepper motor 3, via cable 8. Stepper motor 3 in turn converts the signals to angular movement which is transmitted by substantially rigid spring 13 to the platform 5, thereby indexing the rotation of transducer 11 around the mouth 7 of the coupling to the positional commands of computer 4. Platform 5 rotates upon the cam followers 6 which act to keep it parallel to the mouth 7 of the coupling and transducer 11 correctly aligned as it is positioned by the computer controlled stepper motor 3.

Transducer 11 transmits an ultrasonic acoustical wave from the mouth 7 of the coupling along the longitudinal of the coupling wall 17, substantially parallel to the root of the threads 15. The position of transducer 11 is adjustable with respect to mouth 7 of the coupling thereby making the angle of the transmitted ultrasound adjustable with respect to coupling wall 17.

A constant supply of water is provided by hose 19. The water is distributed through transducer 11 and dispersed between the surfaces of the transducer 11, the mouth 7 of the coupling and the inner surface of the coupling 9 thereby acting as an acoustical couplant of the ultrasonic energy emitted by the transducer to the surfaces of the coupling.

Electrical pulses are sent from the computer 4 to the transducer 11 through cable 18, stimulating the generation of pulses of ultrasonic energy waves by the transducer 11. The transmission of the electrical pulses is timed by the computer 4 and synchronized with the positional signals controlling the movement of the transducer 11 and the common internal clock of the computer 4. As transducer 11 is positioned over a section of coupling wall 17 waves of ultrasound are transmitted along the longitudinal of the corrosponding portion of the coupling wall 17, generally parallel to the root of the threads 15. If there are no defects in the scanned portion of the coupling wall 17 no echos will be detected, the ultrasound continuing unobstructed through the length of the drill collar 16. If a transmitted wave of ultrasound reaches a discontinuity within, or on the surface of the scanned portion of the coupling wall 17 it is reflected back as an echo to the transducer 11 which converts it to an electrical signal and sends it through cable 18 to the computer 4, which in turn calculates the time interval between transmission of the wave and reception of the echo, and records it using the computer's internal clock as a time base reference. The computer 4 correlates this time interval, with the position of the transducer 11 with respect to coupling wall 17. By correlating the position of the transducer 11, and the time interval between transmission of a wave and reception of the echo, the size and position of the defect can be precisely established by the computer 4. In this manner, the computer can reconstruct a two dimensional image of the complete coupling wall 17, revealing not only the depth of any defect but its size and position with respect to the circumference of the coupling wall 17.

The transducer 11 can be rotated 360 degrees around the mouth 7 of the coupling and if desired, can be programmed by the computer 4 to continue to rotate by predetermined percentage.

While the invention has been particularly shown and described with the reference to preferred embodiments thereof, it will be understood by those skilled in the art that the foregoing and other changes in form and details may be made therein without departing from the spirit and scope of the invention.

I claim:

1. An apparatus for ultrasonically inspecting the structural integrity of a drill collar coupling, said apparatus responsive to electrical signals provided by a computer, said apparatus comprising:
   (a) a substantially cylindrical housing;
   (b) a positioning means mounted on a portion of said housing;
   (c) a circular platform disposed adjacent to said housing, a plurality of cam followers mounted symmetrically around said platform, said cam followers having contact surfaces substantially parallel to the top surface of said platform;
   (d) a substantially rigid connecting member joining said positioning means to said platform;

(e) an ultrasonic transducing means for transmitting ultrasonic waves in response to a first electrical signal and receiving echoes of said ultrasonic waves and converting them to a second electrical signal; said transducing means mounted proximate a portion of the arcuate edge of said platform and projecting radially from said edge;

said housing being removably engageable to said drill collar coupling whereby said contact surfaces of said cam followers contact the mouth of said coupling rotatably supporting said platform thereupon.

2. An apparatus for ultrasonically inspecting the structural integrity of a drill collar coupling, said apparatus responsive to electrical signals provided by a computer, said apparatus comprising:

(a) a substantially cylindrical housing open on a bottom end and partially opened in the center of a top end thereof;

(b) a positioning means mounted on the outside center of said top end of said housing;

(c) a circular platform disposed within said housing and positioned substantially parallel to said top end, a plurality of cam followers mounted symmetrically around said platform, said cam followers having contact surfaces substantially parallel to the top surface of said platform;

(d) a substantially rigid connecting member joining said positioning means to said platform, a first end of said member protruding through said partial opening in said top end of said housing and a second end of said member connected to the center of said platform;

(e) an ultrasonic transducing means for transmitting ultrasonic waves in response to a first electrical signal and receiving echoes of said ultrasonic waves and converting them to a second electrical signal; said transducing means mounted proximate a portion of the arcuate edge of said platform and projecting radially from said edge;

said housing being removably engageable to said drill collar coupling whereby said contact surfaces of said cam followers contact the mouth of said coupling rotatably supporting said platform thereupon.

3. The apparatus of claim 1 wherein the positioning means is comprised of a stepper motor.

4. An apparatus for ultrasonically inspecting the structural integrity of the wall of a threaded drill collar coupling, said apparatus responsive to electrical signals provided by a computer, said apparatus comprising:

(a) a substantially cylindrical housing;

(b) a positioning means mounted on a portion of said housing;

(c) a circular platform disposed adjacent to said housing, a plurality of cam followers mounted symmetrically around said platform, said cam followers having contact surfaces substantially parallel to the top surface of said platform;

(d) a substantially rigid connecting member joining said positioning means to said platform;

(e) an ultrasonic transducing means for transmitting ultrasonic waves in response to a first electrical signal and receiving echoes of said ultrasonic waves and converting them to a second electrical signal, said transducing means mounted proximate a portion of the arcuate edge of said platform and projecting radially from said edge; and said housing being removably engageable to said drill collar coupling wall, said contact surfaces of said cam followers contacting the mouth of said coupling whereby said ultrasonic waves are transmitted along the longitudinal of a corresponding portion of said drill coupling and substantially parallel to the root of its threads.

5. A method for inspecting the structural integrity of a threaded drill collar coupling; said method comprising the steps of:

(a) rotatably positioning a transducing means proximate to said drill collar coupling wall;

(b) causing said transducing means to rotate around the circumference of said drill collar coupling wall in response to a first sequence of electrical signals from a computer;

(c) said computer providing a second sequence of electrical signals to said transducing means, said transducing means transmitting pulses of ultrasound along the longitudinal of a corresponding portion of said drill collar coupling and substantially parallel to the root of its threads, in response thereto;

(d) said transducing means receiving echoes of said ultrasound pulses, converting said echoes to a third sequence of electrical signals and transmitting said third sequence of electrical signals to said computer; and (e) said first, second and third sequence of electrical signals being synchronized with an internal timing signal generated by said computer thereby correlating the position of said transducing means with said third sequence of electrical signals to establish the size and position of defects in said drill collar coupling.

* * * * *